United States Patent
Teeny

(10) Patent No.: US 8,668,694 B2
(45) Date of Patent: Mar. 11, 2014

(54) BONE FIXATION ASSEMBLIES AND METHODS OF USE

(76) Inventor: Steven M. Teeny, Gig Harbor, WA (US)

( * ) Notice: Subject to any disclaimer, the term of this patent is extended or adjusted under 35 U.S.C. 154(b) by 886 days.

(21) Appl. No.: 12/135,067

(22) Filed: Jun. 6, 2008

(65) Prior Publication Data

US 2009/0306664 A1 Dec. 10, 2009

(51) Int. Cl.
*A61B 17/72* (2006.01)

(52) U.S. Cl.
USPC .......................................................... 606/64

(58) Field of Classification Search
USPC ................ 606/62–68, 280–299; 623/23.23
See application file for complete search history.

(56) References Cited

U.S. PATENT DOCUMENTS

| | | | | |
|---|---|---|---|---|
| 3,779,240 A | * | 12/1973 | Kondo | 606/282 |
| 4,011,863 A | | 3/1977 | Zickel | |
| 4,103,683 A | * | 8/1978 | Neufeld | 606/67 |
| 4,862,883 A | | 9/1989 | Freeland | |
| 5,300,074 A | * | 4/1994 | Frigg | 606/67 |
| 6,007,536 A | | 12/1999 | Yue | |
| 6,010,505 A | | 1/2000 | Asche et al. | |
| 6,183,475 B1 | * | 2/2001 | Lester et al. | 606/281 |
| 6,221,074 B1 | | 4/2001 | Cole et al. | |
| 6,235,059 B1 | * | 5/2001 | Benezech et al. | 623/17.16 |
| 6,270,499 B1 | | 8/2001 | Leu et al. | |
| 6,533,788 B1 | | 3/2003 | Orbay | |
| 6,572,620 B1 | * | 6/2003 | Schon et al. | 606/62 |
| 6,652,529 B2 | | 11/2003 | Swanson | |
| 6,673,116 B2 | * | 1/2004 | Reiley | 623/21.18 |
| 7,160,302 B2 | | 1/2007 | Warburton | |
| 7,182,765 B2 | | 2/2007 | Roth et al. | |
| 7,867,231 B2 | * | 1/2011 | Cole | 606/64 |
| 2006/0122600 A1 | * | 6/2006 | Cole | 606/62 |
| 2008/0140130 A1 | * | 6/2008 | Chan et al. | 606/280 |
| 2009/0062796 A1 | * | 3/2009 | Parks et al. | 606/62 |
| 2009/0177240 A1 | * | 7/2009 | Perez | 606/86 R |

* cited by examiner

*Primary Examiner* — Jan Christopher Merene
*Assistant Examiner* — Steven Cotroneo
(74) *Attorney, Agent, or Firm* — Baumgartner Patent Law; Marc Baumgartner

(57) ABSTRACT

Intramedullary rod and blade assemblies and methods of implanting said assemblies are disclosed herein. The assemblies provided herein are useful in treating distal, proximal fractures, among other conditions, in large bones including, but not limited to: femurs, tibias, and humeri. Preferred assemblies can include an intramedullary rod having a proximal end and coupling means configured to securely attach to a blade, such that no portion of the rod or the coupling means extend into the fractured fragment beyond the blade. Further preferred assemblies include intramedullary rods that connect in the center of the internal blade, or substantially so, such that the rod and blade form a "T-shape," or substantially so.

8 Claims, 5 Drawing Sheets

BONE FIXATION ASSEMBLIES AND METHODS OF USE

FIELD OF THE INVENTION

The embodiments herein relate to bone fixation assemblies and methods of using said assemblies. More particularly, the teachings herein relate to intramedullary rod and blade assemblies and methods of using these assemblies to treat fractures located near the proximal or distal end of a bone (e.g., femur, tibia) and other orthopedic conditions in patients.

BACKGROUND

Fractures located near the proximal or distal ends of a patient's bone are often problematic for the operating surgeon to fix.

With respect to the femur, proximal fractures commonly occur in the femoral neck, and in the inter-trochanteric region. Distal femur fractures that occur between the femur and the condyles are termed "supracondylar fractures". Distal fractures occurring in one or more of the condyles are termed a "condylar" or "intercondylar" fracture.

Distal femur fractures are often difficult for an orthopedic surgeon to fix because of their proximity to the knee and their frequent association with patients having a total joint replacement covering the end of the bone and/or those suffering from osteoporosis. More specifically, affixing pins, screws, plates, and/or an intramedullary nail in a brittle bone having low mineral density, can often lead to undesirable results.

Prior attempts to treat fractures utilizing an intramedullary nail attached to an internal blade have been described. Prior descriptions are found in U.S. Pat. No. 6,572,620 ("Schon et al.") and U.S. Pat. No. 6,652,529 ("Swanson"), for example. These references are hereby expressly incorporated herein by reference in their entireties.

Schon et al. is directed to methods of affixing two adjoining bones together where the intramedullary nail is implanted into a larger bone (e.g., tibia) and attached to a blade that is positioned into an adjacent smaller bone (e.g., talus). One of the potential disadvantages of the Schon et al. design is that the final configuration is substantially an "L-shape" implant, where the intramedullary nail is secured through a passageway adjacent to the proximal end of the blade (See Schon et al. FIG. 1). One of the disadvantages to the "L-shape" configuration is that it may result in a weaker implant as the intramedullary nail is not centrally secured to the blade, or substantially so. Accordingly, overly long intramedullary nails may be required to maintain the general "L-shape." Another disadvantage to the design taught by Schon et al. is that it is not optimal for treating fractures located near the distal end of a single bone as the coupling mechanism disclosed extends past the lower surface of the blade. This type of coupling mechanism prevents the surgeon from positioning the blade to the more distal parts of the larger bone, where it may be needed for more distal fractures.

In an attempt to address distal femoral fractures, Swanson discloses an intramedullary nail, having a blade passage, configured to receive a blade, wherein the blade passage is located in the proximal end of the nail "some distance" away from the proximal tip of the nail. (See Swanson, col. 6, lines 18-20) Essentially this assembly results in an upside down cross-shape with the proximal end of the intramedullary nail extending past the blade into the distal femur. (See Swanson, FIG. 2). While not being in a general "L-shape" Swanson's design, like that of Schon et al., limits the surgeon's ability to treat fractures located very close to the distal end of the femur, such as condylar and intercondylar fractures. This is because the proximal end of the intramedullary nail extends below the lower surface of the blade, thereby preventing a surgeon from positioning the blade to the more distal parts of the femur. Another disadvantage of the Swanson design is that the distal portion of the intramedullary nail includes a passageway for the blade to pass through. (See Swanson, FIGS. 2 and 3). This passageway is an area of weakness and is more likely to lead to a fatigue fracture of the intramedullary nail. Furthermore, this passageway necessitates a cross-like formation such that the distal tip of the intramedullary nail protrudes past the blade.

In light of the prior art, there is a need in the art for new assemblies and methods for implanting blade and IM nail systems in the distal or proximal end of a patient's bone. Accordingly, one of the objects of the invention is to provide an intramedullary rod and blade assembly that can be implanted more distally or proximally than prior systems and thus fix more distally located fractures on a large bone than the prior art currently allows. A further object of the invention is to provide assemblies that includes an intramedullary nail and blade, each configured to couple with one another without the use of a blade passageway in the intramedullary nail.

SUMMARY OF THE INVENTION

The teachings herein are directed to assemblies for fixing a fractured bone that include an intramedullary nail having proximal and distal ends and is configured to be implanted within an intramedullary canal of the fractured bone, a blade configured to be implanted into a fractured fragment, and having distal and proximal ends, a horizontal plane adjoined by one or more outer flanges, and a central, or substantially central passageway configured to receive means for coupling the blade to the proximal end of said intramedullary nail, and means for coupling the blade to the proximal end of said intramedullary nail configured such that neither said means for coupling nor the intramedullary nail extend past the one or more outer flanges after coupling.

Certain embodiments are directed to a blade passageway that includes a recessed area configured such that after coupling, neither said means for coupling nor the intramedullary nail extend into the fractured fragment past the horizontal plane of the blade. According to preferred embodiments, the one or more outer flanges, extend perpendicularly, or substantially so, to said horizontal plane. In other embodiments, the one or more outer flanges extend at an angle from said horizontal plane.

Further assemblies for fixing a fracture in a bone can include an intramedullary nail having proximal and distal ends and configured to be implanted within an intramedullary canal of the fractured bone, a blade configured to be implanted into a fractured fragment, and having distal and proximal ends, and a central, or substantially central passageway configured to receive means for coupling the blade to the proximal end of said intramedullary nail, and means for coupling the blade to the proximal end of said intramedullary nail configured such that neither said means for coupling nor the intramedullary nail extend into the fractured fragment beyond the blade after coupling.

Further assemblies herein can also include a blade passageway that is an oblong passageway. Furthermore, the blade passageway can be connected to a second aperture on said blade. In more specific embodiments, the second aperture has a larger perimeter than said passageway. Other embodiments include, an external blade plate configured to attach to and secure the proximal end of said blade to the outside of the fractured bone.

Further methods of fixing a fracture in a single bone having an intramedullary canal can include providing an intramedullary nail having proximal and distal ends and configured to be implanted within the intramedullary canal of the fractured bone; providing a blade configured to be implanted into a fractured fragment, and having distal and proximal ends, and a central, or substantially central passageway configured to receive means for coupling the blade to the proximal end of said intramedullary nail, providing means for coupling the blade to the proximal end of said intramedullary nail, positioning said blade into the fractured fragment, positioning said intramedullary nail through an aperture in the blade, and securing said blade to the proximal end of the intramedullary nail with said means for coupling through said central, or substantially central passageway, such that said means for coupling and the intramedullary nail do not extend into the fractured fragment beyond the blade.

According to preferred methods, the aperture in the blade is the central or substantially central passageway configured to receive said means for coupling. According to even more specific embodiments, the aperture in the blade is distinct from and connects to the central or substantially central passageway configured to receive said means for coupling.

Further methods can include a blade that is initially positioned partway across the fractured fragment and after the intramedullary nail is positioned through the aperture, the blade is further positioned such that said intramedullary nail fits within the central, or substantially central, passageway.

BRIEF DESCRIPTION OF THE DRAWINGS

It will be appreciated that the drawings are not necessarily to scale, with emphasis instead being placed on illustrating the various aspects and features of embodiments of the invention, in which.

DETAILED DESCRIPTION OF THE ILLUSTRATED EMBODIMENTS

Figure 1:
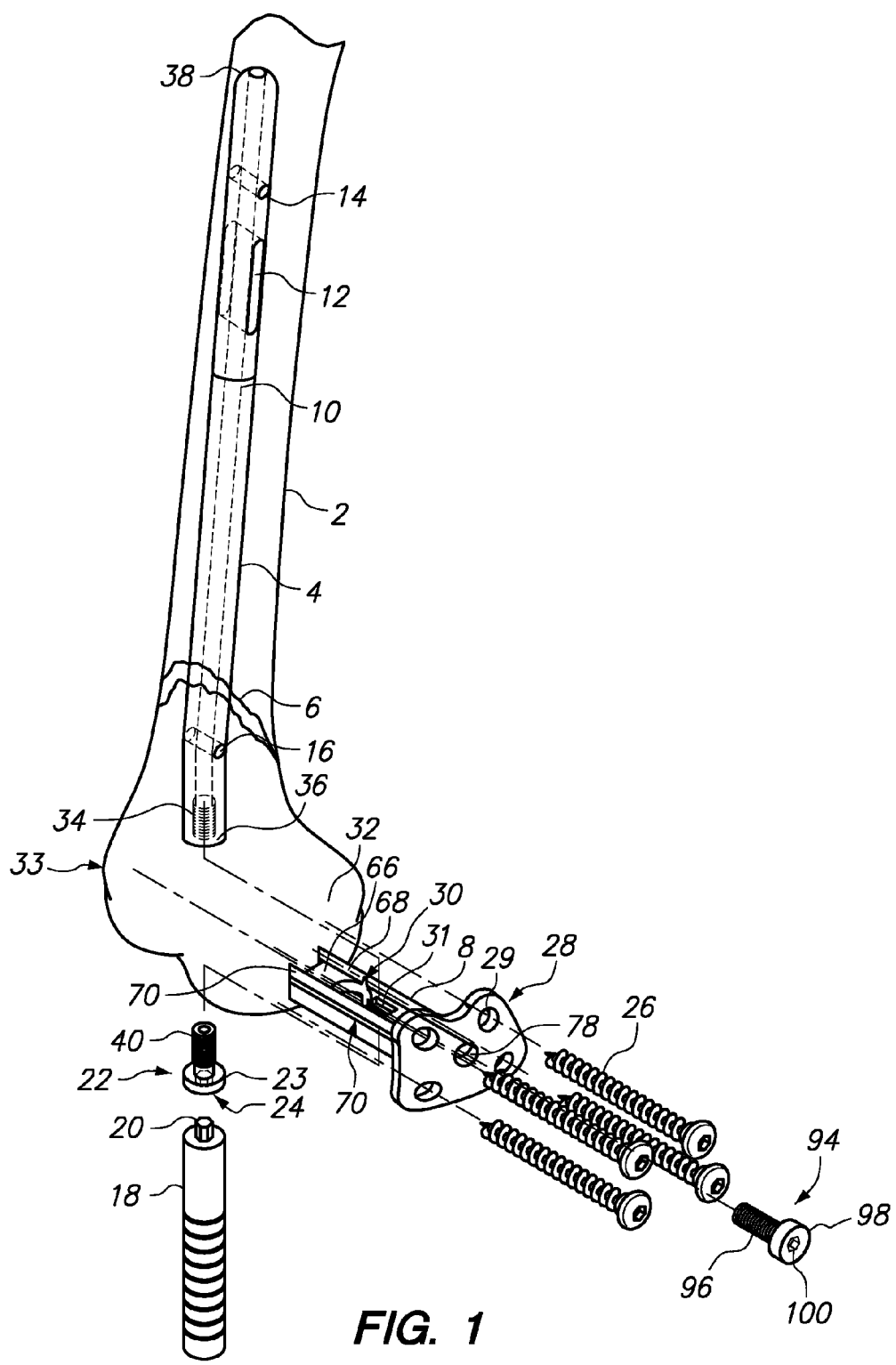
FIG. 1 is an exploded view of a preferred intramedullary rod and blade being positioned in a femoral fracture.
Figure 2:
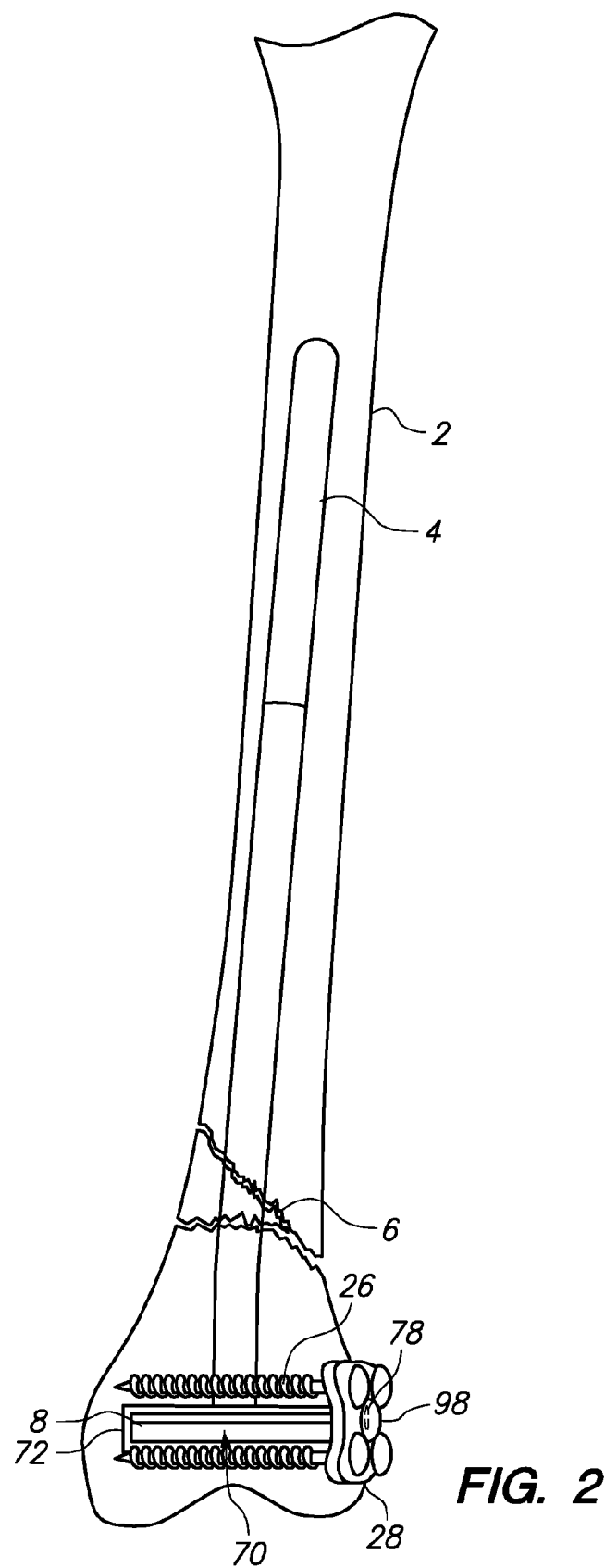
FIG. 2 is a perspective view of a securely coupled preferred intramedullary rod and blade system implanted into a femur.
Figure 3:
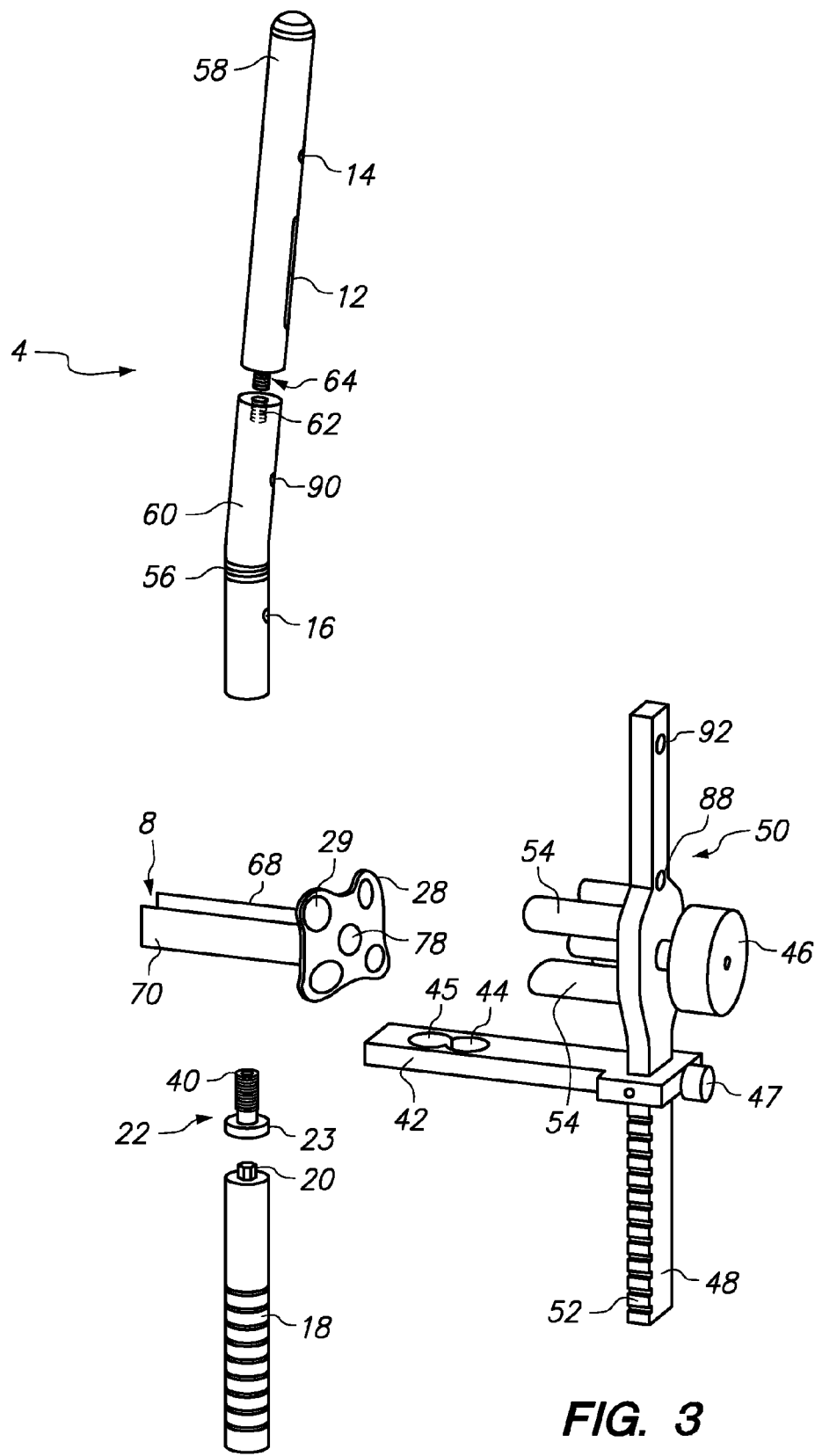
FIG. 3 is a perspective view of an exploded preferred intramedullary rod and blade assembly and outrigger.
Figure 4:
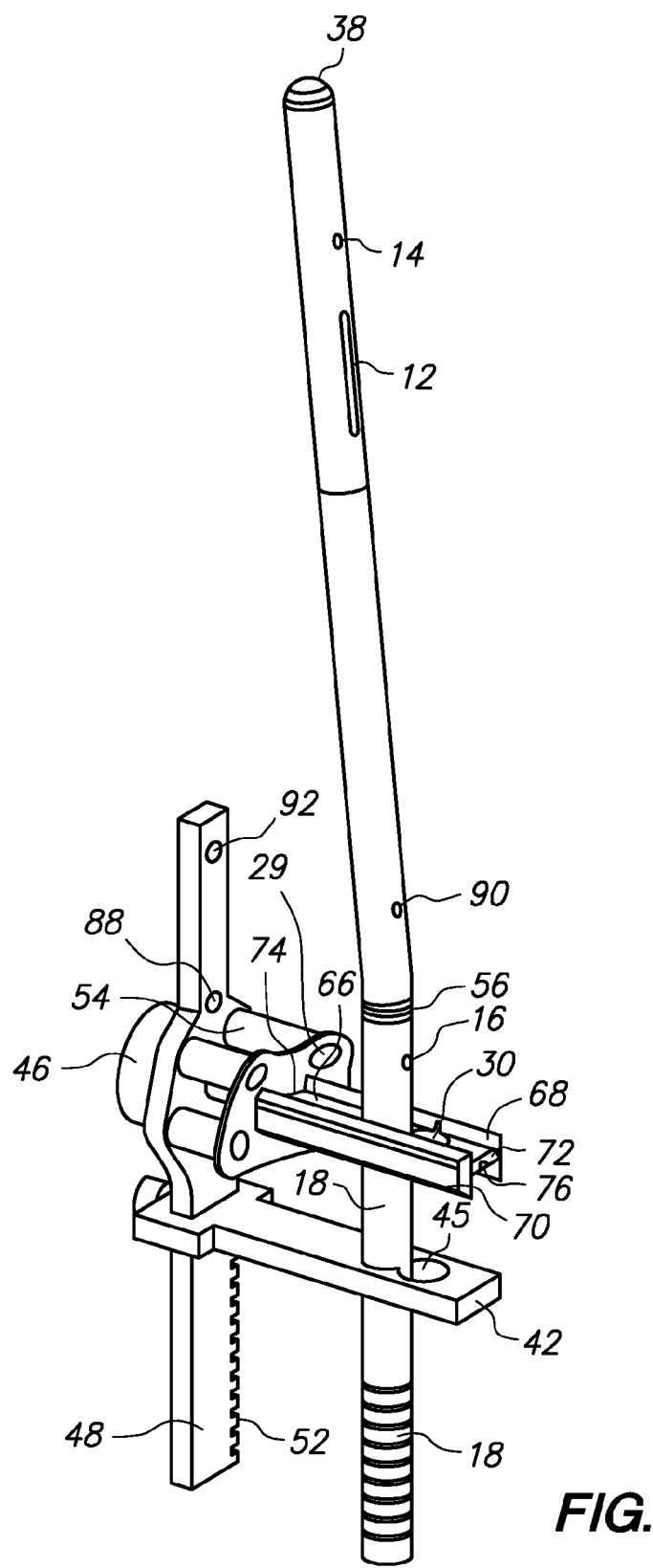
FIG. 4 is a perspective view of an preferred intramedullary rod and blade system and outrigger

Embodiments of the present invention are described below with reference to the above described Figures. It is, however, expressly noted that the present invention is not limited to the embodiments depicted in the Figures, but rather the intention is that modifications that are apparent to the person skilled in the art and equivalents thereof are also included.
Intramedullary (IM) Nail/Rod FIG. 1 depicts an exploded view of a preferred IM nail 4 and blade 8 assembly being positioned in a patient's left femur 2 to treat a fracture 6. As used herein, the terms "intramedullary nail," "IM nail," "intramedullary rod," and "IM rod" can be used interchangeably. The IM nail 4 is preferably configured and selected to be positioned into the patient's medullary cavity of the femur 2 such that it passes through the fractured area 6 of the bone and couples to a blade 8 at its proximal end 36. Accordingly, while the majority portion of the IM nail 4 should extend in a straight line, in preferred embodiments, the IM nail 4 as a whole is coronally angled so that it can be more easily inserted into the medullary canal. The IM nail 4 can also be sagitally angled to match the usual angle subtended by the shaft of the femur and the transverse plane of the knee. In more specific embodiments, the vertex 56 of the angle is preferably positioned near the proximal end 36 of the IM nail 4. The angle at the vertex 56 can vary depending on the particular condition of the patient. Preferred angle degrees can be 8-15°, for example. The position of a preferred vertex 56 on the IM nail 4 is depicted in FIGS. 3 and 4. FIG. 3 depicts the correct orientation of an assembly for insertion into a patient's left femur, while FIG. 4 depicts the same assembly, rotated for illustrative purposes and not oriented for implantation into the left femur.

Likewise, the size and shape of the IM nail 4 can be readily configured to meet a particular patient's needs. Factors that may effect the size and shape of the IM nail 4, non-exclusively include: the size and type of bone structure, the onset of osteoporosis, the age of the patient, and the number and types of fractures, the presence of other implants in the bone, or the presence of a total knee replacement, for example. The following are non-exclusive ranges of preferred dimensions for the IM nail 4. The length of the IM nail from its top (i.e., distal) end 38 to its bottom (i.e., proximal) end 36 is preferably 200-500 mm in length. Furthermore, the IM nail 4 preferably has a diameter of 10-20 mm. Preferred materials that the IM nail 4 can be constructed from non-exclusively include metals such as titanium and stainless steel, ceramics, plastics, composites, and combinations thereof, for example.

According to preferred embodiments, the IM nail 4 includes an internal guide wire channel 10, that traverses along an interior vertical axis of the IM nail 4 and opens at the distal nail tip 38 and the proximal end 36. The guide wire channel 10 has a smaller diameter than the IM nail 4, and is configured to allow the IM nail 4 to be passed along a guide wire 84 for insertion into the femur 2. The proximal end 36 of the IM nail 4 preferably includes a threaded section 34 configured to receive a threaded locking bolt 22, or otherwise configured to be secured to means for connecting to the blade 8.

According to preferred embodiments, the IM nail 4 is constructed as a single piece; alternatively it can be a modular implant. While the Figures are directed to a 2-piece modular IM nail, it is preferred that a single piece IM nail is used with the systems and methods described herein. A 2-piece modular IM nail 4 is depicted in an exploded view in FIG. 3, for example. With respect to FIG. 3, the IM nail is divided into an upper member 58 and a lower member 60 that are configured to be attached to each other. Any suitable means for coupling can be used to attach the upper and lower members 58 and 60, however, according to certain embodiments, the lower end of the upper IM nail member 58 includes a threaded section 64 configured to be screwed into a complementary threaded section 62 positioned at the upper end of the lower IM nail member 60, such that the 2 members can be securely fastened together, forming a stable and strong IM nail 4 before being implanted into a patient in need. Both threaded sections 62 and 64 can include an aperture configured to allow the internal guide wire channel 10 to vertically traverse the length of the IM nail 4, and connect the openings at the top end 38 and bottom end 36. (See FIG. 1)

According to more specific embodiments, in addition to being configured to be secured to the blade 8, the IM nail 4, can also include other means for being secured to the patient's bone, depending on the particular patient's condition. Further means for securing the IM nail 4 can include 1 or more of the following: a locking hole 14, a compression/distraction slot 12, and a stabilization hole 16, for example. Preferably, the upper member 58 of the IM nail includes a locking hole 14 and a compression/distraction slot 12, while the lower member 60 of the IM nail includes 1 or more stabilization holes 16.

Screws, pins, or other means can be inserted into the 1 or more above-described holes and slots, from either a sagittal or coronal plane to more securely set the IM nail 4 in the patient's intramedullary channel. The number of means for securing the IM nail 4 can vary depending on the condition of the particular patient, including but not limited to the size and type of bone structure, the onset of osteoporosis, the age of the patient, and the number and type of fractures, for example. Examples of securing means are known in the art, such as in U.S. patent application Ser. No. 11/250,498, Publication No. 2007/0100342 A1 to Green et al., which is expressly incorporated herein by reference in its entirety. Means for securing the IM nail 4 within the IM canal can non-exclusively be made from stainless steel or titanium, for example.

According to highly preferred embodiments, the IM nails provided herein expressly do not include a blade passage, as shown in U.S. Pat. No. 6,652,529 to Swanson. The exclusion of the blade passage is highly advantageous as it allows for a lower connection of the blade 8 to the IM nail 4 because it does not necessitate that a portion of the IM nail extends below the blade 8. The option to position the blade 8 as low as possible in the femur 2 is advantageous as it allows a surgeon to treat the most distal fractures. It is not desirable to have the blade 8 inserted and positioned above a distal fracture in the femur. If not positioned below, there would be no fixation of the distal fragment and the fracture would remain unstable. The exclusion of a blade passage in the IM nail is also helpful in that the size and shape of the blade and/or blade guide is not dependent on the size and shape of the blade passage in the IM nail. For example, with respect to Swanson, the width of the blade is limited by both the width of the IM nail and the blade passage. Accordingly, a variety of sizes and shapes of blades can more easily be interchanged with a single type of IM nail following the teachings herein. Finally, the inclusion of a blade passage can compromise the strength of the IM nail, and may necessitate increasing the diameter of the IM nail around the blade passageway to prevent a fatigue fracture in the nail or to otherwise strengthen the nail. (See Swanson, col. 5, lines 60-66).

Blade

Figure 6:
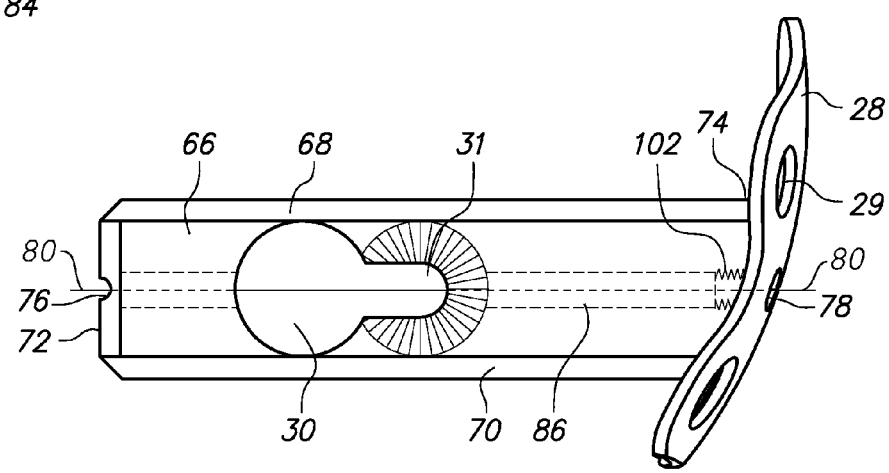
FIG. 6 is a perspective view of a preferred blade.

Preferred blades 8 are configured to coronally enter the condylar area of the femur 2 below or at the fracture site 6 and securely couple to an IM nail 4. A preferred blade 8 having a distal end 72 and a proximal end 74, and blade plate 28, are shown in detail in FIGS. 1, 4, and 6, for example.

While different shapes and sizes of blades 8 can be used with the teachings herein, the preferred shape is like that of an I-beam (i.e., double-T beam), such that the blade has an "H-shaped" cross-section. In general, preferred blades include a horizontal plane 66 flanked by 1 or more outer flanges 68 and 70 that extend perpendicularly (i.e., vertically), or substantially so, above and below the horizontal plane 66. According to more preferred embodiments, when inserted into the femur 2, the horizontal plane 66 defines a transverse plane, or substantially so, while the two flanges 68 and 70 define coronal planes, or substantially so.

According to other embodiments, the blades herein can non-exclusively include two flanges that extend above and below the horizontal plane, one flange that extends above and below the horizontal plane, one flange that extends only above the horizontal plane, one flange that extends only below the horizontal plane, two flanges that only extend above the horizontal plane, or two flanges that only extend below the horizontal plane, for example. According to other embodiments, the blades do not include a horizontal plane, but are rather in the shape of an arch, that preferably bends downwards towards the fractured fragment.

The horizontal plane 66 preferably has a thickness of 2 mm or substantially so, but other thicknesses, non-exclusively including between 1.5-4.0 mm are also contemplated herein, for example. According to more specific embodiments, the thickness of the horizontal plane is greater than the thickness of the locking bolt's head 23. According to even more specific embodiments, no part of the locking bolt 22 extends below the blade's horizontal plane 66 when secured to the IM nail 4. For these embodiments, the horizontal plane 66 can include a recessed area for the bolt's head 23.

The 1 or more outer flanges 68 and 70 preferably, but non-exclusively, can extend 5-8 mm upward and 5-8 downward from the horizontal plane 66, or substantially so. In more specific embodiments, the 1 or more outer flanges 68 and 70 extend downward from the horizontal plane 66 at a distance greater than the length of head 23 of the locking bolt 22. According to these preferred embodiments, no part of the locking bolt 22 extends below the blade's flanges 68 and 70 when it is secured to the IM nail 4. According to non-preferred embodiments, the means for connecting the blade to the IM nail can extend a minimal distance below the flanges 68 and 70.

According to preferred embodiments, the blades provided herein are not screws or pins, and thus do not have a circular or substantially circular cross-section, and do not include threads. Blades 8 preferably include one or more guide pin channels 86 of sufficient diameter to allow passage of a guide pin 80 and that has openings at the distal end 76 and proximal end 78. According to other embodiments, the blade 8 can include two guide pin channels, preferably parallel to one another.

Preferred blades 8 can be configured to have lengths from the proximal end 74 and the distal end 72 such that they extend across the full width of the bone, or substantially so, as measured from the lateral cortex to the medial cortex. Alternatively, blades 8 can be configured to have lengths from the proximal end 74 to the distal end 72 less than the width of the bone, such as 5-10 mm less, as measured from the lateral cortex to the medial cortex. Accordingly, by example, a preferred blade 8 coronally inserted through the lateral epicondyle 32, will have a distal terminus 72 that does not traverse the entire width of the femur 2, and more preferably is 5-10 mm from the medial epicondyle 33.

Preferably, the blade 8 includes one or more passages through its main body, or horizontal plane 66, configured to allow the connecting means to pass through to secure the blade 8 to the IM nail 4. With respect to more specific embodiments, a blade can include a circular, oblong, or other shaped aperture, and the IM rod 4 can be impacted directly through this hole and secured therein with said connecting means. In more preferred embodiments, the blade 8 can include a larger aperture that feeds or tapers into a smaller aperture that functions as a final socket for the IM rod 4. For example with reference to FIG. 6, the IM rod 4 can initially be positioned through the larger aperture 30; afterwards, the blade 8 can be manipulated (e.g., impacted) such that the IM Nail 4 is positioned into the adjoining socket 31, to create a tighter fit and to secure with connecting means.

In more specific embodiments, when a tapered aperture or socket 31 is provided, said aperture 31 is centrally located on the main body, or horizontal plane 66 of the blade, or substantially so. In other embodiments, said aperture 31 is expressly not located near the proximal or distal ends 74 and 72 of the blade 8. The above configurations are advantageous as it allows for a T-shaped connection, or substantially so, between the IM rod 4 and the blade 8, as opposed to an "L-shaped" implant, or substantially so. The teachings herein are expressly not directed to "L-shaped" or substantially "L-shaped" blade and IM nail final assemblies, such as those disclosed in U.S. Pat. No. 6,572,620 to Shon et al., for example. The objective of utilizing the L-shaped implants in Shon et al. is to fix two adjacent bones together, while the teachings herein are directed to treating a single fractured bone. The disadvantages of the L-shaped implants in fixing a fractured single bone are discussed in detail above.

Preferred connecting means for securing the IM nail 4 to the blade 8 include a locking bolt 22 having a threaded shaft 40 that is configured to be screwed into threads 34 located at the bottom (i.e., proximal) end 36 of the IM nail 4. According to preferred embodiments where the blade includes a larger aperture 30 that feeds or tapers into a smaller aperture 31 that functions as a final socket for the IM rod 4, the connection means (e.g., locking bolt 22, pin, lock, plug, washer) are not configured to pass through the larger aperture 30 to connect said IM rod 4 to said blade 8, but rather are configured to pass through said socket 31 to secure said IM rod 4 to the blade 8.

According to preferred embodiments, when the means for connecting the blade to the IM nail are secured, (e.g., locking bolt 22, pin, latch, coupling member, etc.) no portion of the IM nail 4 or the connecting means protrude below either of the 1 or more vertical flanges 68 and 70 of the blade. In other advantageous embodiments, when secured, no portion of the IM nail 4 or means for connecting the IM nail 4 to the blade 8 extends below the horizontal plane 66 of the blade 8. For example, when a locking bolt 22 is screwed into the threaded portion of the IM nail 34, no portion of IM nail 4 or the locking bolt 22, such as the head 23, or a washer, extends below the 1 or more vertical flanges 68 and 70. As another example, when a locking bolt 22, is secured into place, no portion of the IM nail 4 or the locking bolt 22, such as the head 23 or a washer, extends below the horizontal plane 66 of the blade 8. According to non-preferred embodiments, a minimal portion of the connecting means can extend below the horizontal plane 66 and/or flanges 68 and 70.

The aperture 31 on the blade can be threaded or not, but is preferably not, such that the threads 40 of the locking bolt 22 do not screw securely into the blade 8. For embodiments where the blade's aperture 31 is threaded, the locking bolt 22 would screw securely into the blade 8. For these embodiments, it can be advantageous to have the head of the locking bolt threaded and complementary to threads within the blade's aperture. The head 23 of the locking bolt 22 preferably includes means that allow the threads 40 of the locking bolt 22 to be rotated into the threads 36 of the IM nail 4 such that the blade 8 is securely attached to the IM nail 4. More specifically, the head can include a receptacle 24 configured to be tightened and/or loosened by a screwdriver or wrench of the following non-exclusive head shapes: Phillips, flathead, square, star-shaped, square shape, or a hexagonal wrench shape (e.g., Allen wrench).

According to alternative embodiments, the locking bolt 22 can be cannulated, or not. For example, the receptacle 24 can be an opening for a cannula that extends through the threaded section of the bolt 40 to an opening positioned at the end opposite from the head 23. Embodiments that include a cannula are advantageous in that they allow the bolt 22 to slide along a guide wire 84 to align up with the blade 8 and IM nail 4, in order to secure said implants. These embodiments are non-exclusively of particular advantage for situations where the fracture is mobile, and/or the IM nail 4 has moved away from the blade 8. Threading a cannulated bolt 22 through a guide wire 84 ensures that the bolt 22 will lead to the threaded section 34 of the IM nail 4.

FIG. 1 depicts a screwdriver 18 having a hexagonal shaped head 20 configured to be received in the locking bolt's 22 receptacle 24. As mentioned above, depending on the shape of the receptacle 24, other tightening means including wrenches and screwdrivers having the complementary head shape can be used to rotate the locking bolt 22 into and out of the IM nail 4. A "Tommy bar" can also be added (not shown) perpendicularly positioned at, or near the opposite end of the head 20 such that it forms a "T-shape" or cross-shape. In certain embodiments, the screwdriver 18 or wrench can also be cannulated along its longest axis and have a diameter sufficient to thread a guide wire 84 through. If a "Tommy bar" is utilized, it can also include a passage to allow the guide wire 84 to perpendicularly pass through.

Preferred blades 8 provided herein include or are coupled to an external blade plate 28. There are multiple ways of attaching the blade 8 to the external blade plate 28, non-exclusively including utilizing screws, pins, snaps, and/or latches, for example. According to preferred embodiments a blade bolt 94 can be positioned through a hole 78 in the plate 28 to secure the blade 8. For example, the bolt 94 preferably includes a threaded end 96 that is complementary to a threaded end 102 within the blade 8. The head 98 of the blade bolt 94 preferably includes a receptacle 100 for a wrench or screwdriver, or other means to allow the surgeon to screw the bolt 94 into the blade's threaded area 102. In other embodiments, the blade 8 and blade plate 28 are a single piece, and are constructed as such.

Preferred blade plates 28 are configured to anchor the blade 8 to the outside of the femur 2, and thus can be contoured with respect to the outer femur 2, where it can be secured. The blade plates 28 described herein can include 1 or more (e.g., 2, 3, 4, 5, or 6) apertures 29, or alternative means, to allow means for securing the blade plate 28 and thus the attached blade 8 to the outer femur. Preferred means include the use of screws 26 that can engage with the plate to secure it to the outside of the femur 2, such as the lateral cortex, or the lateral epicondyle 33, for example. According to various embodiments, the means for securing the blade plate 28 to the outer femur (e.g., screws, pins) can be slightly longer than the length of the blade 8 from the proximal end 74 to the distal end 72, the same length, or shorter. Preferred means (e.g., screws 26) are the same length of the blade 8, and would have a length equivalent to the distance from the lateral cortex to the medial cortex, or substantially so.

Method

The following are preferred methods for implanting the IM nail 4 and blade 8 assemblies provided herein. General methods for treating a distal or proximal fracture in a large bone are provided with specific emphasis on treating a distal femoral fracture. Those with skill in the art can readily utilize the teaching herein to treat fractures in other large bones.

The patient is preferably placed in a supine position on a radiolucent table. Means for elevating the patient's knee are placed under the patent leg, such as a triangle, padded bar, or bolster, and are preferably radiolucent. According to preferred embodiments, the patient's knee can be flexed at about 45-75 degrees. A radiation (e.g., x-ray) emitting and detection device, such as a C-arm, or other type of imaging device, is preferably directed to the patient's fractured bone. The imaging device, using anterior/posterior and/or lateral images, can be used to determine gross fracture alignment. Other devices and methods can also be used to determine the alignment of the fracture.

After gross fracture alignment is determined, the surgeon can make an incision on the lateral side of the leg, or location where the blade will be implanted (e.g., lateral epicondyle 32). The dissection can be carried down to the level of the lateral condyle. Preferably with the assistance of the imaging device, a surgeon can insert a guide pin 80 across the distal fragment, for the femur this would be parallel to the knee, or substantially so. The guide pin 80 can be inserted in the condylar region, depending on the location and type of fracture. For extremely distal fractures, the guide pin 80 can be placed 1.5-2 cm above the intercondylar notch, as can be determined by imaging. If a total knee replacement is in place, the guide pin 80 can be inserted approximately 1 cm above the pegs, or 1 cm above the box, in a posterior cruciate substituting total knee arthroplasty. The guide pin 80 can preferably traverse the entire length of the bone and reach the medial cortex.

A depth gage can be used to measure the size of blade 8 that is needed. In advantageous embodiments, the blade 8 is configured such that the distal end 72 terminates at the side of the bone opposite from the side of entry, or substantially so, including within 10 mm (e.g., 5-10 mm) from the opposite side of the bone. For example, if the blade 8 is inserted coronally from the lateral cortex or epicondyle, its distal end will preferably terminate at the medial epicondyle or cortex, or alternatively within 10 mm before the medial epicondyle, or medial cortex.

The surgeon can form a coronal, or substantially so, blade 8 channel through the bone, such as the femur. Many ways of forming said channel are possible, including chiseling, drilling, punching, boring, and combinations thereof, for example. Preferably, the surgeon utilizes a starting chisel to coronally impact ⅓ of the way across the width of the bone, such as the femur. If the bone surrounding the desired area for forming the blade channel is osteoporotic, the surgeon may forgo the use of the chisel and coronally impact the blade 8 itself through the targeted bone. The surgeon may now impact the blade across the distal fragment from lateral to medial, until the hole 30 is at the level of the intercondylar notch. This will be when hole 45 in the outrigger is also in line with the intercondylar notch. Guide pins may be also now placed through holes 54 in the guide, and then screws 26 placed over the guide pins.

According to preferred embodiments, a longitudinal midline or slightly medial incision can be made from the patella to the tibial tubercle. This incision can be 5-8 cm, for example. A medial parapatellar incision can additionally be made to expose the intercondylar notch. An alternate deep incision can be longitudinally made in the patellar tendon.

Figure 5:
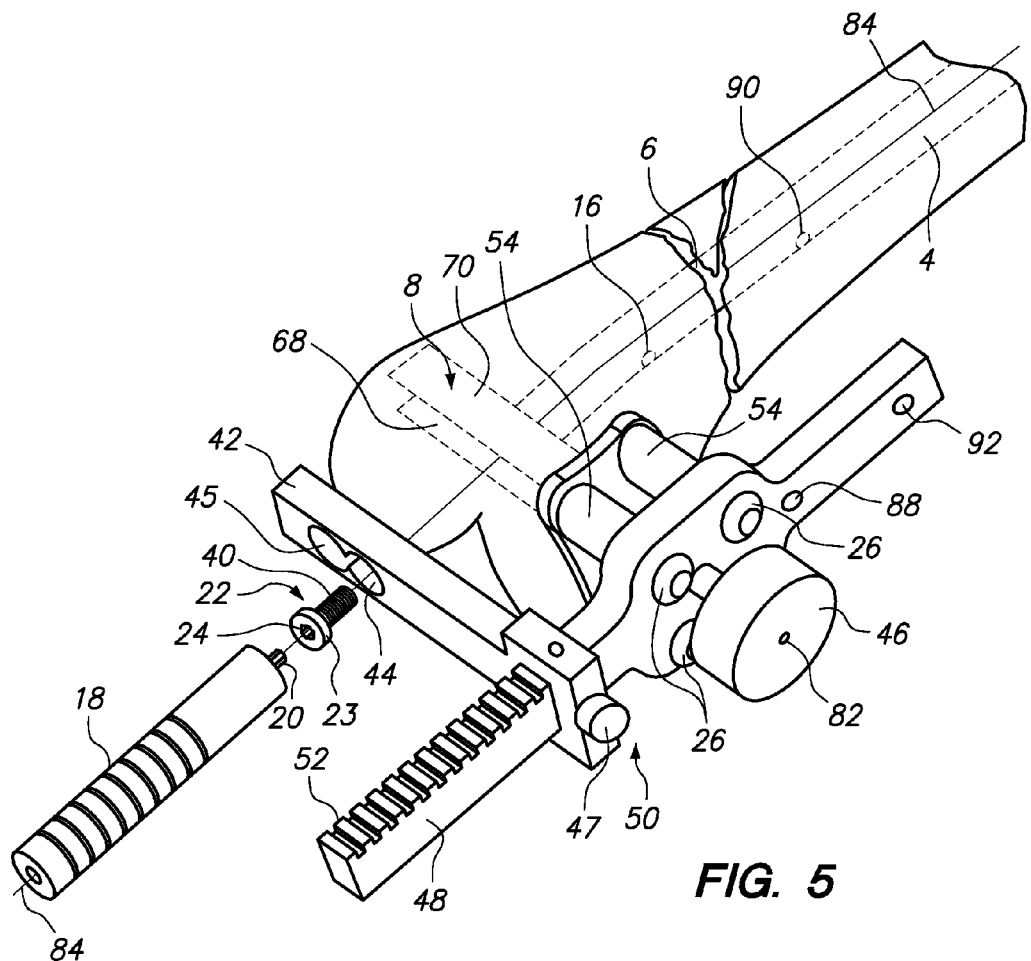
FIG. 5 is a perspective view showing a preferred outrigger and an intramedullary rod and blade system.

An outrigger 50 and impactor 46 can be positioned at the surgical site, as non-exclusive means for guiding, aligning, positioning, and implanting the assemblies provided herein. Other means for the above functions can be used in conjunction with or instead of the described outrigger 50 and impactor 46 with the teachings herein. FIG. 5, shows a preferred position of the outrigger 50 and impactor 46 with respect to a fractured femur. Any suitable impactor 46 can be used with the teachings herein. Preferably, the impactor includes a channel 82 configured to allow a guide pin 80 to pass through, in order to align the blade 8. Preferably, the channel 82 is aligned with the channel 86 channel opening 78 within the blade. In further embodiments, the impactor 46 includes two channels that align with two guide pin channels within the blade.

The guide bar 42 is perpendicular to, or substantially so, and is adjustable along an extension 48 of the outrigger 50, that extends parallel, or substantially so, to the targeted bone (e.g., femur), and preferably past the distal fragment. The guide bar 42 can include 1 or more apertures. According to more preferred embodiments, the guide bar 42 includes two apertures, preferably adjoining, such as indicated by the apertures 44 and 45 in FIG. 3, for example. While described as two apertures, alternative configurations also allow for a single oblong, or oval shape aperture, for example. Preferably, the first and second apertures 45 and 44 are connected such that they form an outline of a "figure-8", or substantially so.

A means for adjustably sliding the bar 42 at defined intervals along the extension 48 is preferably provided. One such example is providing teeth 52 on the extension 48, and an adjustable knob 47 on the guide bar 42. More specifically the knob 47 can be unscrewed to loosen the attachment between the bar 42 and the extension 48. The bar 42 can then be slid along the extension 48 to the desired position, and the knob 47 can then be screwed to tighten the connection. Other means for adjustably sliding the bar 42 along the extension 48 include the use of stops, detents, latches, flanges, release mechanisms, and the like. While a method of adjustment is shown using teeth in FIG. 3-5, continuous means (e.g., non-teethed extension) for adjustably sliding the bar 42 along the extension 48 are also contemplated in alternative embodiments.

The outrigger 50 can further include one or more distal holes (e.g., 88 and 92) that are configured to align with one or more compression/distraction slots, locking holes, and/or stabilization holes (e.g., 16 and 90) on the IM nail 4. For example, with reference to FIG. 4, the first distal hole 88 aligns with stabilization hole 16 on the IM nail 4 and the second distal hole 92 aligns with a second stabilization hole 90 on the IM nail 4. The above alignment allows the surgeon to place one or more pins through the outrigger's distal holes and into the corresponding IM nail's holes to prevent movement of the IM nail 4 as the means for coupling (e.g., locking bolt 22) are positioned to secure the blade 8.

The surgeon can create a hole configured to allow a guide sleeve and guide wire 84 into the proximal aspect of the IM canal of the targeted bone 2. A guide sleeve configured to sheath a guide wire 84 for the IM nail 4 can be placed through the first aperture 45 on the outrigger's guide bar 42 and up to the surface of the targeted bone, such that the tip of the guide sleeve is positioned just below the area in the bone where the blade 8 will be impacted into. The blade 8 is then impacted by pounding on the impactor 46 until the first hole 30 within the blade 8 is aligned just above the tip of the guide sleeve, which is preferably positioned at the center of the distal fragment, or the intercondylar notch of the femur 2. Once aligned with first hole 30 within the blade 8, the guide wire 84 can then be passed through the sleeve, and then once the fracture is aligned, into the proximal fragment.

The guide sleeve can then be removed, and means for expanding the diameter of the medullary canal can be used to make space for the IM rod 4. Preferred means include flexible reamers, for example. According to preferred embodiments, assuming the bone is of normal strength, the medullary canal can be expanded to have a diameter approximately 1 mm larger than the diameter of the selected IM rod 4. A ruler, or other measuring device, can be used to measure the distance from the blade 8 to the proximal metaphyseal region of the targeted bone (e.g., femur) in order to determine the length of an IM rod 4 appropriate for stabilizing the fracture 6. The IM rod 4 can then be impacted through the first hole 30 and in the blade 8. Preferably, the IM rod 4 can pass over the guide wire 84, though the first hole 30, into the IM canal, until the entire IM rod 4 is passed such that its proximal end 36 is positioned just superior to the blade 8.

The blade 8 can then be adjusted (e.g., further impacted) until the guide wire 84 is aligned through the socket 31 and second aperture 44 in the guide bar 42. A screwdriver 18 can be used to secure a locking bolt 22, or other coupling means, to connect the blade 8 to the IM rod 4. The one or more distal holes on the outrigger 88 and 92 are preferably aligned with the one or more stabilization holes, 16 and 90 respectively, in the IM rod 4. A temporary pin, or other means for securing, can be placed through the one or more distal holes (88 and 92) and into their aligned stabilization holes 16 and 90 to prevent the IM rod 4 from rotating, such as when the locking bolt 22, or other means for coupling the blade 8 to the IM rod 4 is tightened and secured. Additional blade screws 26 can also can be positioned through their respective holes 29 to secure the blade plate 28 and blade 8 to the distal fragment. Additionally, a blade bolt 94 can be positioned through a hole 78 in the plate 28 to secure the blade 8. The outrigger 50 and impactor 46 can be removed after the system is securely implanted.

While preferred embodiments have been directed to treating distal femoral fractures, the systems and methods provided herein can readily be useful with respect to osteotomies (e.g., distal femur, proximal femoral, proximal tibia, distal tibia, proximal humeral), talotibial fusions, knee fusions, proximal femoral fractures, proximal humeral fractures, and proximal and distal tibial fractures. For methods of treating proximal fractures the terminology of proximal and distal fractures provided above can be reversed.

What is claimed is:

1. An assembly for fixing a fractured bone comprising:
   an intramedullary nail having a length of 200-500 mm between proximal and distal ends and configured to be implanted within an intramedullary canal of the fractured bone;
   a blade configured to be implanted into a fractured fragment, and having distal and proximal ends, a horizontal plane, and a passageway positioned centrally, or substantially centrally between the distal and proximal blade ends, and configured to receive means for coupling the blade to the proximal end of said intramedullary nail, wherein the central or substantially central blade passageway is connected to a second aperture on said blade that is not centrally or substantially centrally positioned on the blade and has a larger perimeter than said central, or substantially central passageway and is configured to allow the distal end of the intramedullary nail to pass through; and
   means for coupling the blade to the proximal end of said intramedullary nail configured such that neither said means for coupling nor the intramedullary nail extend vertically past the horizontal plane of the blade after coupling.

2. An assembly for fixing a fracture in a single bone comprising:
   an intramedullary nail configured to be implanted within an intramedullary canal of the fractured bone and having a length of 200-500 mm between proximal and distal ends and lacking a passageway configured to receive a blade;
   a blade configured to be implanted into a fractured fragment, and having distal and proximal ends, and a passageway positioned centrally or substantially centrally between the distal and proximal ends of the blade and configured to receive means for coupling the blade to the proximal end of said intramedullary nail, and wherein said passageway is configured to allow the distal end of the intramedullary nail to pass through and is connected to a second aperture on said blade; and
   means for coupling the blade to the proximal end of said intramedullary nail that are configured to couple through said central, or substantially central, passageway.

3. The assembly of claim 2, further comprising an external blade plate configured to attach to and secure the proximal end of said blade to the outside of the fractured bone.

4. A method of fixing a fracture in a single bone having an intramedullary canal comprising:
   providing an intramedullary nail having proximal and distal ends and configured to be implanted within the intramedullary canal of the fractured bone;
   providing a blade configured to be implanted into a fractured fragment, and having distal and proximal ends, and a passageway centrally, or substantially centrally positioned between the distal and proximal ends of the blade, and configured to receive means for coupling the blade to the proximal end of said intramedullary nail;
   providing means for coupling the blade to the proximal end of said intramedullary nail;
   inserting said blade at least partially into the fractured fragment;
   inserting said intramedullary nail through an aperture in the blade after the blade has been at least partially inserted into the fractured fragment; and
   securing said blade to the proximal end of the intramedullary nail with said means for coupling through said central, or substantially central passageway, such that said means for coupling and the intramedullary nail do not extend into the fractured fragment beyond the blade.

5. The method of claim 4, wherein said aperture in the blade is the central or substantially central passageway configured to receive said means for coupling.

6. The method of claim 4, wherein said aperture in the blade is distinct from and connects to the central or substantially central passageway configured to receive said means for coupling.

7. The method of claim 6, wherein said blade is initially positioned partway across the fractured fragment; after the intramedullary nail is positioned through the aperture, the blade is further positioned such that said intramedullary nail fits within the central, or substantially central, passageway.

8. An assembly for fixing a fracture in a single bone comprising:
   an intramedullary nail configured to be implanted within an intramedullary canal of the fractured bone and having proximal and distal ends and lacking a passageway configured to receive a blade;
   a blade configured to be implanted into a fractured fragment, and having distal and proximal ends, and a passageway positioned centrally or substantially centrally between the distal and proximal ends of the blade and configured to receive means for coupling the blade to the proximal end of said intramedullary nail, and wherein said passageway is configured to allow the distal end of the intramedullary nail to pass through and is connected to a second aperture on said blade;
   an external blade plate configured to attach to and secure the proximal end of said blade to the outside of the fractured bone; and
   means for coupling the blade to the proximal end of said intramedullary nail that are configured to couple through said central, or substantially central, passageway.

* * * * *